United States Patent [19]

Eichhorn

[11] Patent Number: 5,030,422

[45] Date of Patent: Jul. 9, 1991

[54] SMOG CONTROL SYSTEM

[76] Inventor: Cathy D. S. Eichhorn, 15145 Lassen St., Mission Hills, Calif. 91345

[21] Appl. No.: 428,778

[22] Filed: Oct. 30, 1989

[51] Int. Cl.$^5$ .............................................. A62B 11/00
[52] U.S. Cl. ...................................... 422/121; 422/5; 422/22; 422/123; 422/169; 422/170; 422/186; 422/188; 422/231
[58] Field of Search .................... 422/5, 13, 22, 121, 422/24, 123, 169, 184, 186, 261, 305, 306, 170, 124, 231, 188

[56] References Cited

U.S. PATENT DOCUMENTS

| | | |
|---|---|---|
| 3,178,255 | 4/1965 | Neuwald et al. ............... 422/121 |
| 3,885,929 | 5/1975 | Lyan et al. ..................... 422/169 |
| 3,941,670 | 3/1976 | Pratt, Jr. ......................... 422/22 |
| 4,244,712 | 1/1981 | Tangret .......................... 422/121 |
| 4,265,747 | 5/1981 | Capa et al. ..................... 422/24 |
| 4,370,301 | 1/1983 | Doi et al. ....................... 422/122 |
| 4,400,355 | 8/1983 | Donnelly et al. .............. 422/170 |
| 4,550,010 | 10/1985 | Chela ............................ 422/4 |
| 4,750,917 | 6/1988 | Fujii .............................. 422/24 |
| 4,780,277 | 10/1988 | Tanaka et al. ................. 422/4 |
| 4,861,558 | 8/1989 | Lehto ............................ 422/106 |

Primary Examiner—Robert J. Warden
Assistant Examiner—Lynn Kummert
Attorney, Agent, or Firm—Robert J. Schaap

[57] ABSTRACT

In a smog control system comprising a plurality of fans or blowers which are located to introduce air into a smog particle destruction chamber operated with lazer energy. The smog particles are broken down and the air is passed into a filtering chamber which may preferably adopt the form of a liquid charcoal chamber. The air may be preferably bubbled through the liquid charcoal and the effluent may then be passed into a freshening agent chamber where a freshening agent may be added to the air. The air may then pass as an effluent from the freshening agent chamber. A liquid charcoal supply may be connected to the liquid charcoal chamber and the recovered liquid charcoal which has been spent may be reused for other purposes.

14 Claims, 1 Drawing Sheet

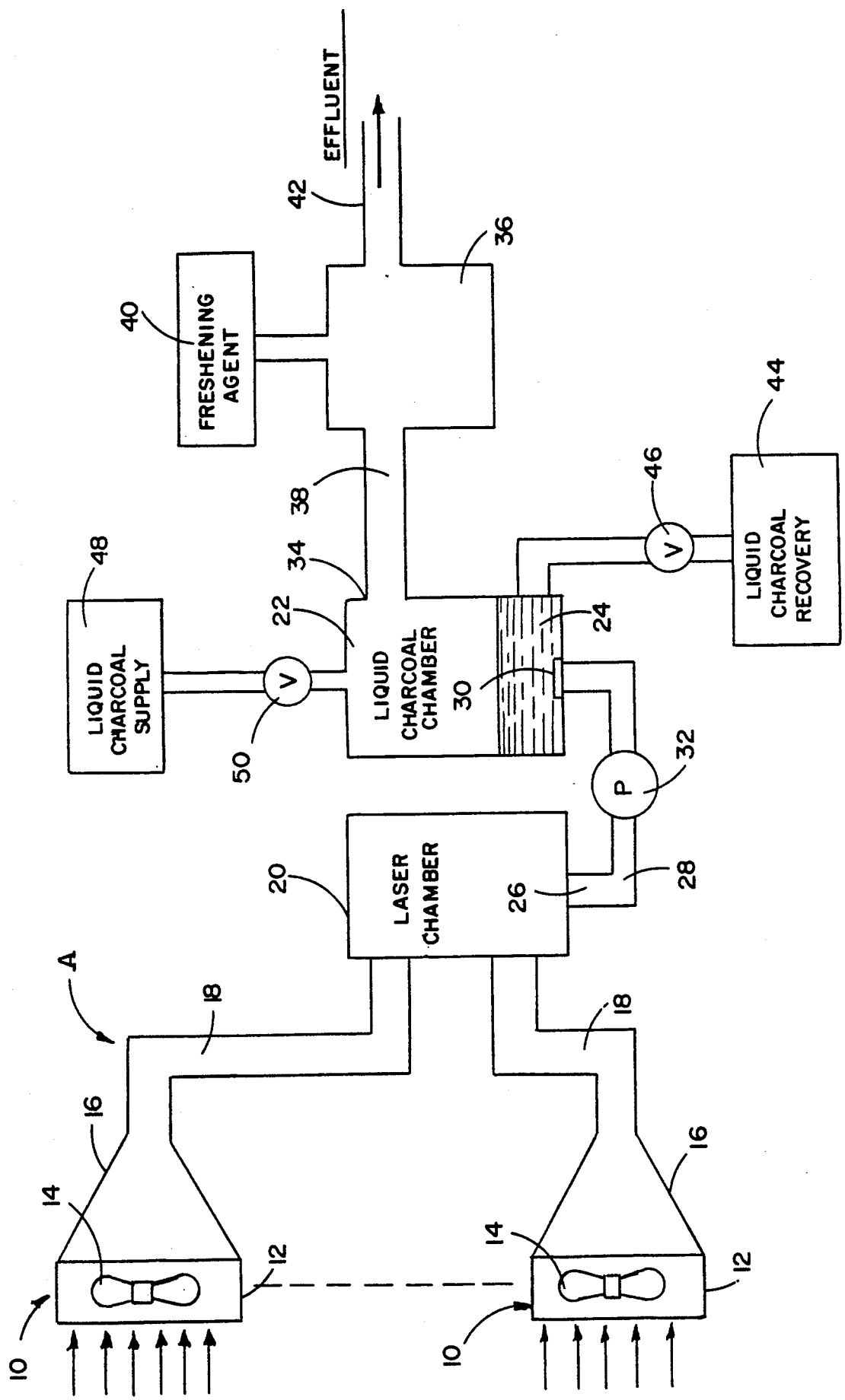

SMOG CONTROL SYSTEM

BACKGROUND OF THE INVENTION

1. Field of the Invention

This invention relates in general to certain new and useful improvements in a smog control system, and more particularly, to a smog control system which utilizes lazer technology for breaking down the smog particles and then filtering contaminants from the air and adding a freshening agent thereto.

2. Brief Description of the Prior Art

In recent years, smog pollution has become a very serious and pronounced problem, particularly with the burning of hydrocarbon combustion fuels. Thus, for example, automotive vehicles, upon which much of the industrialized world population is heavily dependent, are a major contributing factor to the smog pollution. In like manner, burning of various hydrocarbon combustion fuels for heating and other purposes is a significant contributing factor.

Further, smog is generated as a result of various industrial processes, many of which have little or no effective means for reducing the smog generation in the industrial process. Hence, there is a very widespread and long felt need to reduce smog density, particularly in urban environments.

The high concentrations of smog in many urban atmospheres and for that matter, many areas where human and animal occupation exists, has given rise to a substantial increase in health problems. For example, there have been several recognized links between high smog concentration in air and incidence of lung cancer. As a result of the increased health problems, many governmental agencies have attempted to impose restrictions on gaseous effluents from industrial plants and the gaseous exhaust from automotive vehicles and the like. However, these restrictions have not been effective in reducing the high concentration of smog in normal breathing air. Therefore, there is a recognized need for governmental agencies to take a positive role in reducing the smog content.

OBJECTS OF THE INVENTION

It is, therefore, one of the primary objects of the present invention to provide a smog control system which utilizes lazer energy for breaking down smog particles and a filtering means for removing certain contaminants from air.

It is another object of the present invention to provide a smog control system of the type stated which utilizes fans or blowers for introducing smog containing air into a lazer chamber and which air is then introduced into a liquid charcoal filtering chamber.

It is a further object of the present invention to provide a smog control system of the type stated in which a freshening agent can be added to the relatively smog free air.

It is an additional object of the present invention to provide a smog control system of the type stated where the liquid charcoal can be recycled and used for other purposes.

It is also an object of the present invention to provide a method for removing smog from normal breathing air by using lazer energy for breaking down the smog particles.

With the above and other objects in view, my invention resides in the novel features of form, construction, arrangement and combination of parts presently described and pointed out in the claims.

BRIEF SUMMARY OF THE INVENTION

The present invention relates to a smog control system and more specifically, to a smog reduction system which is designed to reduce the concentration of smog contaminants in the air.

The present invention utilizes a plurality of fans or blowers which are designed to introduce smog ladden air into a break-down chamber. This break-down chamber, in a preferred embodiment of the present invention, utilizes lazer energy. Thus, when the air is introduced into the lazer chamber, lazer energy will be used to literally break down the smog particles into other particles which do not have the same deleterious effects. Any conventional means for generating the lazer energy may be employed. Accordingly, the exact lazer generating means is neither illustrated nor described in any further detail herein.

The air, in which the smog particles have been broken-down, is then passed into a filtering chamber. In a preferred embodiment of the present invention, the filtering chamber contains liquid charcoal. In this case, the air is preferably bubbled through a bath of the liquid charcoal. The air is then passed through the liquid charcoal chamber into a freshening agent chamber wherein a freshening agent, such as a lemon freshening agent, or other freshening agent could be used for addition to the air in order to provide a certain desired aroma. The effluent of the freshening agent chamber is then returned to the normal ambient environment.

In accordance with the present invention, the charcoal chamber may be connected to a suitable source of liquid charcoal which may be periodically introduced into the liquid charcoal chamber. In like manner, a liquid charcoal recovery vat may also be connected to this chamber for receiving the spent liquid charcoal so that the latter could be recycled and used for other industrial or commercial purposes.

This invention possesses many other advantages and has other purposes which may be made more clearly apparent from a consideration of the forms in which it may be embodied. These forms are shown in the drawing forming a part of and accompanying the present specification. They will now be described in detail for the purposes of illustrating the general principles of the invention, but it is to be understood that such detailed description is not to be taken in a limiting sense.

BRIEF DESCRIPTION OF THE DRAWINGS

Having thus described the invention in general terms, reference will now be made to the accompanying drawing (one sheet) in which:

The FIGURE as shown is a schematic illustration showing a smog control system constructed in accordance with and embodying the present invention.

DETAILED DESCRIPTION OF A PREFERRED EMBODIMENT

Referring now in more detail and by reference characters to the drawing which illustrates a preferred embodiment of the present invention, A designates a smog control system comprising a plurality of blowers 10, each of which acts as a type of exhaust fan for drawing air into blower housings 12. The air drawn into each of the housings 12 is then moved by fan blades 14 into funnel shaped outlets 16 connected to each of the blower housings 12.

In the embodiment of the invention, as illustrated in the FIGURE, only two such blowers 10 are illustrated. However, it should be understood that any number of blowers could be employed in accordance with the present invention. The number of blowers which are employed and the overall size of the blowers would depend upon the actual size of the remaining components in the smog control system and the ability to handle the quantity of air which is drawn by the blowers. Moreover, the positioning of the blowers would also be based upon the quality of the air at the point of use and the ability to optimize the efficiency of the overall smog control system.

The air which is moved into the funnel shaped outlets 16 is carried by conduits 18 into a smog particle breakdown chamber 20. In the preferred embodiment of the invention, this breakdown chamber adopts the form of a chamber which utilizes lazer energy for breaking down the smog particles. Thus, the break-down chamber 20 is often referred to as a "lazer chamber".

As indicated previously, any means for generating lazer energy may be used in connection with the present invention. For this reason, no specific lazer generating mechanism has been shown or described herein.

The lazer chamber 20 is designed so that the air which is introduced therein will be subjected to lazer beams which are dispersed throughout the entire chamber. These lazer beams are effective in actually breaking down these smog particles. The vast majority of the smog particles which have been found to be concentrated in normal air are capable of being broken down into smaller and other particles by the lazer beams. Moreover, these other particles have been found to be far less harmful than the basic smog particles found in smog ladden air.

After the air has been subjected to lazer energy treatment in the lazer chamber 20, the air is then passed into a filter chamber 22 which contains a suitable filter medium. In this case, the filter medium is a bath of liquid charcoal 24. The liquid charcoal filter has been found to be highly effective in removing many of the particles contained in the air and thus, serves as an excellent filter means.

The air which is introduced into the filter chamber 22 may be introduced in such manner that it is passed over the liquid filter bath 24, or otherwise, it may be bubbled through the bath, in the manner as shown. In this case, the air is drawn from an outlet 26 at the bottom of the lazer chamber and through a transfer pipe 28 and introduced into the bottom wall of the liquid charcoal chamber 22. A trap 30 may be located at the point of entry of the transfer pipe 28 to prevent any of the liquid contained in the chamber 22 from passing into the pipe 28. However, the trap 30 is designed so that the air can pass freely into the liquid charcoal chamber 22.

For purposes of effectuating the transfer of the air from the lazer chamber 20 to the liquid charcoal chamber 22, a pump 32 may be disposed within the transfer pipe 28. The pump may not be absolutely necessary, inasmuch as there will be a positive pressure on the air in the chamber 20 by virtue of the action of the blowers 10. Nevertheless, the pump P would be effective in providing a driving force for moving the air efficiently into the chamber 22.

Air may pass from an outlet 34 at the liquid charcoal chamber 22 into a freshening agent chamber 36. The transfer from the liquid charcoal chamber 22 to the air freshening chamber 36 occurs through another transfer conduit 38. A freshening agent may be introduced into the freshening agent chamber 36 from a freshening agent supply source 40. In this case, the amount of the freshening agent introduced into the chamber 36 could be regulated by any suitable control means (not shown). The freshening agent would be introduced into the chamber 36 in order to provide a freshening ingredient to the air. For this purpose, a lemon freshening agent or the like may be employed. Naturally, the freshening agent chamber 36 is not necessary in accordance with the present invention, but is believed to be highly effective for providing a desired fragrance or aroma to the air.

The freshening chamber 36 has an outlet port 42 for discharge of the treated air back into the ambiant atmosphere. This effluent from the port 42 effectively provides completely freshened and cleansed air.

Spent liquid charcoal can be drawn from the liquid charcoal chamber 22 and introduced into a liquid charcoal recovery vat 44. A suitable control valve 46, as illustrated in the FIGURE, would control the outlet from the liquid charcoal chamber.

A liquid charcoal supply source 48 is also provided for metering liquid charcoal into the liquid charcoal chamber 22 through a metering valve 50. In this case, the two valves 46 and 50 could be ganged for a common operation so that the amount of liquid charcoal introduced into the chamber 22 is proportional to the amount of liquid charcoal drawn from that chamber on a periodic basis. Moreover, the valves 46 and 50 could be designed for either manual operation or automatic operation. Thus, and in a preferred embodiment, the valves 46 and 50 would be designed to withdraw a selected amount of liquid charcoal from the chamber 22 over a predetermined time interval, based on the amount of air which is passed through the liquid charcoal chamber 22.

Thus, there has been illustrated and described a unique and novel smog control system which is capable of reducing smog particles to relatively non-harmful particles and removing those particles from an air stream and which thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations, and other uses and application which do not depart from the spirit and scope of the invention are deemed to be covered by the invention.

Having thus described the invention, what I desire to claim and secure by Letters Patent is:

1. A smog control system for breaking down harmful smog components in an air stream removing those components, said system comprising:
   a) a smog particle break-down chamber,
   b) means for forcibly moving air into the smog particle break-down chamber,
   c) means for generating laser energy and means for introducing the laser energy into the break-down chamber, wherein the laser energy is present in an intensity for breaking down smog particles into smaller particles which are substantially less harmful than the original smog particles and without substantially chemically affecting the air molecules.

d) a filter chamber positioned and arranged to receive the output of the break-down chamber and containing a filter medium therein for providing only a filtering action to remove certain smog particles, and e) an effluent means positioned and arranged for discharging the filtered air to the ambient atmosphere.

2. The smog control system of claim 1 further comprising means for introducing the output of the filter chamber into a freshening chamber in which a freshening agent is mixed with the air and the air containing the freshening agent is then discharged through the effluent means to the ambient atmosphere.

3. The smog control system of claim 2 further comprising a freshening agent supply source connected to the freshening chamber for introducing a freshening agent therein on a periodic basis.

4. The smog control system of claim 1 further comprising means for introducing the air from the break-down chamber into a liquid filter medium in the filter chamber.

5. The smog control system of claim 4 further comprising means for bubbling the air from the break-down chamber through the liquid medium in the filter chamber.

6. The smog control system of claim 5 further comprising a transfer pipe connecting a lower end of the break-down chamber to a lower end of the filter chamber.

7. The smog control system of claim 6 further comprising a pumping means located in the transfer pipe for moving air from the break-down chamber to the filter chamber.

8. The smog control system of claim 1 wherein the filter medium is liquid charcoal.

9. The smog control system of claim 8 further comprising means for removing the liquid filter medium from the filter chamber and depositing the medium in a liquid filter medium recovery vat.

10. The smog control system of claim 9 further comprising means for adding the liquid filter medium to the filter chamber on a proportional basis according to the amount of liquid filer medium removed therefrom.

11. The smog control system of claim 10 further comprising a first control valve means for controlling the amount of liquid filter introduced into the liquid filter chamber and a second control valve means for controlling the amount of liquid filter medium withdrawn from the liquid filter chamber.

12. A smog control system for breaking down harmful smog components in an air stream and removing those components, said system comprising:

a) a smog particle break-down chamber, b) means for forcibly moving air into the smog particle break-down chamber, c) means for generating laser energy and means for introducing the laser energy into the break-down chamber, wherein the laser energy is present in an intensity for breaking down smog particles into smaller particles.

d) a filter chamber positioned and arranged to receive the output of the break-down chamber and containing a liquid filter medium therein for removing certain smog particles.

e) an effluent means positioned and arranged for discharging the filtered air to the ambient atmosphere, f) means for withdrawing the liquid filter medium from the filter chamber and depositing the medium in a liquid filter medium recovery vat, g) means for adding liquid filter medium to the filter chamber on a proportional basis according to the amount of liquid filter medium removed therefrom, and h) a first control valve means for controlling the amount of liquid filter introduced into the liquid filter chamber and a second control valve means for controlling the amount of liquid filter withdrawn from the liquid filter chamber.

13. The smog control system of claim 12 further comprising means for introducing the output of the filter chamber into a freshening chamber in which a freshening agent is mixed with the air and means for discharging the air containing the freshening agent through the effluent means to the ambient atmosphere.

14. The smog control system of claim 12 wherein the filter medium is liquid charcoal.

* * * * *